United States Patent

Oftring et al.

[11] Patent Number: 5,025,103
[45] Date of Patent: Jun. 18, 1991

[54] GLYCEROL AMINOCARBOXYLATES AND PREPARATION AND USE THEREOF

[75] Inventors: Alfred Oftring, Duerkheim; Stefan Birnbach; Rolf Fikentscher, both of Ludwigshafen; Richard Baur, Mutterstadt; Alexander Kud, Eppelsheim; Ulrich Goeckel, Boehl-Iggelheim; Johannes Perner, Neustadt, all of Fed. Rep. of Germany

[73] Assignee: BASF Aktiengesellschaft, Ludwigshafen, Fed. of Rep. of Germany

[21] Appl. No.: 467,204

[22] Filed: Jan. 19, 1990

[30] Foreign Application Priority Data

Jan. 20, 1989 [DE] Fed. Rep. of Germany ....... 3901613

[51] Int. Cl.$^5$ .......................................... C07C 229/26
[52] U.S. Cl. .................................... 560/170; 560/171; 560/151
[58] Field of Search .................. 560/170, 171, 151

[56] References Cited

U.S. PATENT DOCUMENTS

| | | | |
|---|---|---|---|
| 4,021,359 | 5/1977 | Schwab | 560/170 |
| 4,330,677 | 5/1982 | Linke et al. | 560/170 |

FOREIGN PATENT DOCUMENTS

| | | | |
|---|---|---|---|
| 0287885 | 2/1988 | European Pat. Off. | 500/170 |
| 0287846 | 3/1988 | European Pat. Off. | 560/170 |
| 6468344 | 3/1989 | Japan | 560/171 |
| 1444874 | 8/1976 | United Kingdom | 560/170 |

*Primary Examiner*—James H. Reamer
*Attorney, Agent, or Firm*—Oblon, Spivak, McClelland, Maier & Neustadt

[57] ABSTRACT

Glycerol aminocarboxylates of the formula

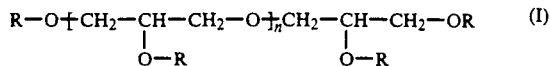

where
n is from 0 to 10 and
R is

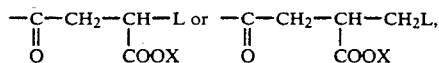

where
L is iminodiacetate, aspartate, glutamate, sarcosinate, glycinate, serinate, hydroxyaspartate, ethanolaminoacetate, diethanolamino, alanate or taurinate and
X is hydrogen, an alkali metal, ammonium or substituted ammonium,
are prepared by esterifying glycerol or polyglycerols which contain up to 10 glycerol units with maleic anhydride or itaconic anhydride and addition of compound L-H where L is as defined above to the double bonds of the esters, and are used as complexing agents.

7 Claims, No Drawings

GLYCEROL AMINOCARBOXYLATES AND PREPARATION AND USE THEREOF

US-A-4,021,359 discloses detergent formulations which contain from 5 to 50% by weight of a detergent and a builder prepared by virtually complete esterification of for example pentaerythritol, sorbitol or mannitol with maleic anhydride and neutralization of the esterification products.

GB-B-1,444,874 discloses a detergent composition in which the phosphates have been wholly or partly replaced by reaction products obtained by esterification of at least trihydric alcohols or saccharides with dicarboxylic anhydrides and subsequent neutralization of the esterification products and which have at least three ester groups. EP-A-0,287,885 discloses inter alia the use of serine-N,N-diacetic acid and derivatives thereof as complexing agents for heavy metal and/or alkaline earth metal ions.

It is an object of the present invention to make available more effective complexing agents for heavy metal and alkaline earth metal ions which besides having a strong complexing effect are ecologically safe.

We have found that this object is achieved according to the present invention by glycerol aminocarboxylates of the formula

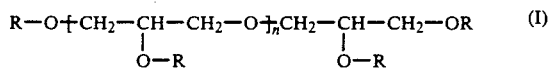

where
n is from 0 to 10 and
R is

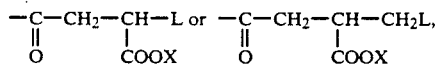

where
L is iminodiacetate, aspartate, glutamate, sarcosinate, glycinate, serinate, hydroxyaspartate, ethanolaminoacetate, diethanolamino, alanate or taurinate and
X is hydrogen, an alkali metal, ammonium or substituted ammonium.

The compounds of the formula I are obtainable by esterifying
(a) compounds of the formula

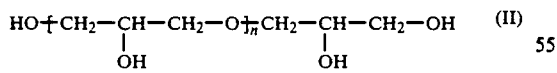

where n is from 0 to 10, with
(b) maleic anhydride, itaconic anhydride, a maleic half-ester or an itaconic half-ester to give compounds of the formula

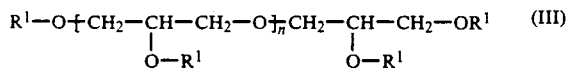

where
R¹ is

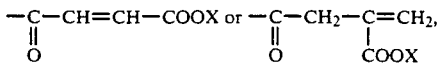

where X is as defined in claim 1, and then reacting the compounds of the formula III with compounds of the formula $$L-H \quad (IV)$$

where L is as defined in claim 1, in a weakly alkaline aqueous medium to give compounds of the formula I.

In the first stage of the reaction to prepare the compounds of the formula I according to the present invention, the above-indicated compounds (a) are reacted with (b). The compounds of the group (a) can be characterized by means of the formula
where n is from 0 to 10, preferably from 1 to 4. Suitable compounds (a) are for example glycerol, diglycerol triglycerol, tetraglycerol, pentaglycerol, hexaglycerol, heptaglycerol, octaglycerol and decaglycerol. Preference is given to those polyglycerols of the formula II where n is from 1 to 4. Polyglycerols of the type defined are known. They are prepared by condensation of glycerol at from about 200° to 250° C. This condensation reaction is preferably catalyzed by the presence of acids or bases. It produces polyglycerols which may still contain up to about 20% by weight of glycerol and also polyglycerols having higher degrees of condensation. The viscosities of the polyglycerols thus obtainable is about 500–1,500 mPas. The condensation products have OH numbers of from 1,500 to 1,000 mg of KOH/g.

Suitable compounds of group (b) are maleic anhydride, itaconic anhydride and the half-esters of maleic acid and itaconic acid which are each derived from monohydric $C_1$-$C_4$-alcohols, e.g. monomethyl maleate, monoethyl maleate, mono-n-propyl maleate, monoisopropyl maleate, mono-n-butyl maleate, monoisobutyl maleate and the corresponding half-esters of itaconic acid.

The reaction of compounds of groups (a) and (b) to give the compounds of the formula

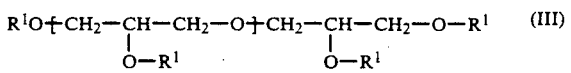

where
R¹ is

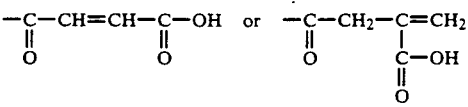

is carried out a from 80° to 140° C. The esterification of compounds (a) is preferably carried out in the presence of an esterification catalyst, for example sodium acetate. Per OH mole equivalent of (a) it is customary to use from 0.05 to 1.5, preferably from 1 to 1.1, moles of a compound (b). The preparation of apolyglycerol and the esterification of the polyglycerol with a compound (b) is preferably cacrried out in a single reaction vessel by first condension glycorol therein at from 200° to 250° C., then cooling down the polyglycerol to a temperature within the range from 80° to 140° C., preferably from 100° to 120° C., and thereafter esterifying the polyglycerol by addition of the above-stated amount of a compound of group (b) in the absence of solvents and preferably with the exclusion of water. A particularly preferred way of carrying out the esterification is for example to meter the maleic anhydride in under the surface of the hot polyglycerol at 80°-140° C. For this ensures virtually complete suppression of any sublimation of the maleic anhydride. This procedure gives conversions of more than 90%. Complete reaction is obtained by stirring the reaction mixture for a certain time, for example 1-2 hours, at the stated reaction temperatures after the maleic anhydride has been added. On cooling to below 50° C., the compounds of the formula III solidify as a glassy mass. However, at 80°-100° C. the compounds of the formula III are still readily stirrable. To ensure convenient handling of the compounds of the formula III, sufficient water is added to the melt of the compounds of the formula III within the temperature range from 80° to 130° C. as to obtain clear 50-80% strength ty weight aqueous solutions of the compounds of the formula III. Surprisingly, virtually no hydrolysis of the ester functions takes place when aqueous concentrated solutions of the compound of the formula III are prepared in this way, although the preparation takes place at from 80° to 130° C. Particular preference, on account of the very good biodegradability, is given to polyglycerol aminocarboxy-lates which are obtainable by esterification of compounds of the abovementioned formula II with maleic anhydride at 80°-140° C. with the exclusion of water, the addition of water to from 50-80% strenght by weight solution, and reaction with glutamic acid.

If maleic or itaconic half-esters are used in the esterification of the compounds (a), the customary transesterification catalysts, for example titanium tetraalkyl compounds, are used and the particular $C_1$-$C_4$-alcohols formed in the course of the transesterification of the maleic or itaconic half-esters are distilled continuously out of the reaction mixture. Particular preference is given to the preparation of compounds of the formula III where virtually all OH groups of the parent compounds of group (a) have been esterified and where the esterification has been carried out with maleic anhydride or a maleic half-ester. To prepare these compounds, the compounds of the formula II are preferably reacted with maleic anhydride or a mono-$C_1$-$C_4$-alkyl maleate using from 1 to 1.5 mole equivalents of maleic anhydride or mono-$C_1$-$C_4$-alkyl maleate poer OH equivalent of compound II.

The compounds of the formula I according to the present invention are obtained in a second stage of reaction by reacting the compounds of the formula III with the compounds of group (c). Group (c) includes amines and amino acids of the structure L—H. Suitable compounds of group (c) are for example ethanolamine, diethanolamine, iminodiacetic acid, asparagic acid, glutamic acid, ethanolaminoacetic acid, hydroxyasparagic acid, sarcosine, glycine, serine, taurine and laurine. Of the compounds mentioned, iminodiacetic acid and glutamic acid are preferred.

The addition of compounds (c) to the double bonds of the compounds of the formula III takes place in aqueous solution. For this addition reaction the compounds (c) are used in such an amount that from 0.5 to 1.3 mole equivalents of amine or amino acid of the structure L—H, preferably from 0.9 to 1.1 mole equivalents, are used per mole equivalent of double bonds in the formula III. Since the compounds of the formula III are already present in aqueous solution, the individual components can be brought together in ay desired manner. For instance, aqueous solutions of compounds of the formula III and aqueous solutions of compounds of group (c) can each be metered separately into a reaction vessel where they are reacted. However, it is also possible first to introduce aqueous solutions of compounds of the formula III into a reaction vessel and to add the compounds of group (c) batchwise or continuously. This procedure permits convenient inspection and control not only of the temperature but also of the pH. Preferably, in the second stage of the preparation of the compounds according to the present invention, at least one compound of component (c) is introduced first and the aqueous solution of the compounds of the formula III is added under controlled conditions. The reaction preferably takes place in a weakly alkaline medium at pH 8-11, preferably pH 9-10. The reaction temperature is from 10° to 70° C., preferably from 15° to 40° C. It is advantageous to carry out the reaction in a buffered medium. Suitable buffer substances are for example sodium carbonate and sodium acetate.

Since the second reaction stage takes place in an alkaline medium, it is advisable to neutralize the compounds, of the formula III prior to the reaction with compounds (c). The neutralization is preferably carried out at up to 50° C., for example within the range from 0° to 45° C., preferably from 10° to 25° C. The neutralizing agents used are bases, for example alkali metal hydroxide solutions, preferably sodium hydroxide solution or potassium hydroxide solution, ammonia, amines, such as triethylamine, tributylamine, ethanolamine, diethanolamine or triethanolamine, and morpholine. The amount of buffer substance is from 5 to 40, preferably from 10 to 25, mol % of sodium carbonate or sodium acetate based on the total amount of base requied to neutralize the carboxyl groups of the compounds of formula III. The concentration of the solids in the second stage of the preparation of the compounds according to the present invention is from 30 to 70, preferably from 45 to 60, % by weight.

The reaction of the compounds of the formula III and IV gives the compounds of the formula I

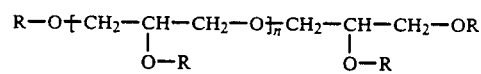

where
n is from 0 to 10, preferably from 1 to 4,
R is

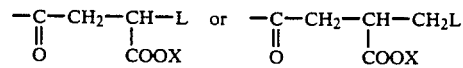

X is a hydrogen, alkalic metal, ammonium or substituted ammonium ion equivalent and
L is

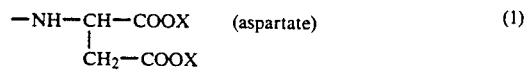 (aspartate) (1)

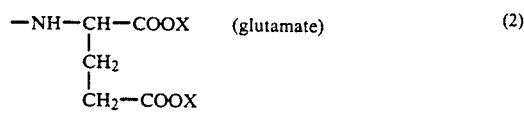 (glutamate) (2)

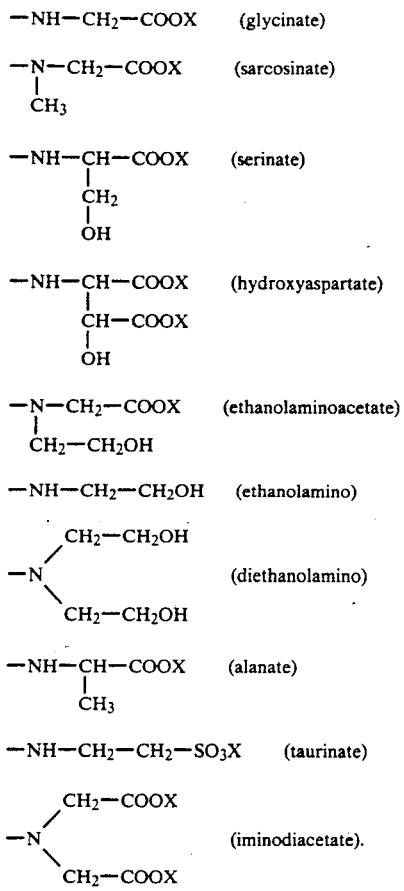

The compounds of the formula I can be modified, for example by the inclusion of sulfo groups. Such compounds are preparable by replacing up to 30% by weight of compound (c) by sulfite or bisulfite, preferably in the form of the sodium or potassium salts. This produces an addition of sodium sulfide or potassium sulfide to the double bond of the ester groups present in compounds III.

A further possible way of modifying the compounds of the formula I according to the present invention comprises esterifying some of the OH groups of the glycerol or polyglycerol, for example up to 30 mol % of the OH groups, with an aliphatic or aromatic carboxylic acid in place of maleic acid or itaconic acid. Suitable for this purpose are for example long-chain carboxylic acids, for example 2-ethylexanoic acid or $C_4$-$C_{18}$ -carboxylic acids, such as stearic acid, or aromatic carboxylic acids, such as phthalic acid. Even partially ethoxylated polyglycerols or glycerol can be used as compounds of group (a) to modify the compounds of the formula I. If a compound of formula II has been ethoxylated, the amount of ethylene oxide is up to 50 mol %.

The glycerol aminocarboxylates of the formula I can be worked up in various ways, for example by converting the sodium salt solutions of the compounds of formula I into the acid form by the addition of sulfuric acid or by the introduction of carbon dioxide. the sodium salts can be obtained directly from the aqueous solutions in pure form by distilling off the water, preferably under reduced pressure, or by spray drying. The salts of the compounds of formula I, for example the sodium salts, can also be isolated by adding to the aqueous solution of the sodium salts of the compounds of formula I from two to three times the amount of a water-miscible organic solvent, for example methanol or acetone. This precipitates the sodium salts, which are then readily isolatable.

The compounds of formula I are used as complexing agents for heavy metal and/or alkaline earth metal ions. The compounds are suitable in particular for complexing calcium, magnesium, iron, copper, nickel and manganese ions. Owing to this property, they can find application in various fields, Their particular advantage is that they are very readily biodegradable compounds. The compounds of the formula I can be used for example as a constituent of redox catalysts to prevent the precipitation in an alkaline medium of the iron salt customarily used as part of redox catalysts.

Besides having a complexing effect, the compounds of the formula I also have a dispersing effect. They can therefore be used as dispersants for finely divided precipitates, in particular as scale inhibitors in water treatment. The amounts used range from about 0.1 to 100 ppm, based on water.

In the photographic industry, the compounds of the formula I can be used in developer and fixing baths prepared from hard water. In these baths, the compounds of the formula I prevent the precipitation of sparingly soluble calcium and magnesium salts. Iron-(III)-complexing agent solutions can advantageously be used in bleach fixing baths as replacement for the ecologically unsafe hexacyanoferrate solutions. The compounds of the formula I according to the present invention can also be used in the textile industry to remove heavy metal traces from natural and synthetic fibers during the manufacturing or dyeing process. This prevents many problems: soil, spots and stripes on the textile material, loss of brightness, poor wettability, and unlevel dyeings. If the compounds according to the present invention are used as complexing agents in the paper industry, they prevent problems due to heavy metal ions, in particular iron ions, during papermaking.

They can also be used as dispersants for pigments, for example in the preparation of aqueous highly concentrated slurries of clays or chalks for use as paper coating compositions.

The compounds of the formula I are also suitable for use as complexing agents in aqueous baths for the chemical deposition of copper. Chemical coppering baths are aqueous solutions which customarily contain a copper salt, formaldehyde, an alkali metal hydroxide and one or more complexing agents with or without further auxiliaries. In such baths, the complexing agent has the purpose to prevent the precipitation of copper hydroxide during coppering and to reduce the concentration of free copper ions to such an extent that any adventitious, wild precipitation of copper is prevented. In addition, the baths may contain for example stabilizers in an amount of from one to a few mg/liter. Such stabilizers are for example sodium cyanide, allylthiourea or 2,2'-dipyridylamine. The coppering temperature range is in general from 15° to 50° C., preferably from 20° to 30° C. Coppering is complete within a period of from 5 to 60, preferably from 10 to 40, minutes. The concentration of complexing agent of the formula (I) in the bath is about 10–40 g/liter of bath liquid. The bath pH is not less than 10. Preferred copper compounds are crystalline copper sulfate and copper(II) chloride. Formaldehyde is added in amounts of from 1 to 12 g/liter. The bath may also contain customary surfactants, as well as the abovementioned stabilizers.

In the Examples, the hydrogenation iodine numbers were determined in accordance with German Standard Specification DIN 53241 part 2. The percentages are by weight. The K values were determined by the method of H. Fikentscher, Cellulosechemie, 13, (1932), 58-64, 71-74, K being $k.10^3$. The measurements were carried out in aqueous solution at 25° C., a pH of 7.0 and a polymer concentration of 1% by weight of the Na salt of the polymers.

EXAMPLES

EXAMPLE 1

(a) Preparation of polyglycerol maleate 185 g of a polyglycerol having an average degree of condensation n=2.8 (OH number=1176 mg of KOH/g) were heated to 120° C. 392 g (4 mol) of liquid maleic anhydride at a temperature of 70° C. were then metered in underneath the surface of the polyglycerol liquid over 2.5 hours under a nitrogen atmosphere. The mixture was then stirred at 120° C. for 1 hour. The result was a yellow oil (analysis: saponification number 788 mg of KOH/g, acid number 4857) to which 250 g of water were added at 100° C. with vigorous stirring. The result was 771 g of a 70% strength aqueous pale yellow solution of a polyglycerol maleate with a saponification number of 774 and an acid number of 451 (each calculated for 100%). The level of free maleic acid by HPLC was 3.9%; hydrogenation iodine number: 186.

(b) Reaction of polyglycerol maleate of 1a with iminodiacetic acid to give polyglycerol maleate iminodiacetate 226 g (1.7 mol) of iminodiacetic acid were suspended in 250 g of water. 289 g of 40% strength aqueous sodium hydroxide solution were added to bring the suspension to pH 10. After 90 g of sodium carbonate had been added, 422 g of the 70% strength polyglycerol maleate solution were added dropwise with vigorous stirring at 10°-15° C. over 45 minutes during which the medium was maintained at pH 10 by the addition of 219 g of 40% strength sodium hydroxide solution. The mixture was subsequently stirred at 25° C. for 2 hours. Analyzed by HPLC, the resulting solution was found to contain as minor components 2.5% of sodium iminodiacetate, 0.5% of sodium fumarate, 1.4% of sodium maleate and, as a saponification product of the polyglycerol maleate iminodiacetate end product, 0.4% of the sodium salt of asparagicdiacetic acid.

Workup: The polyglycerol maleate iminodiacetate product can be precipitated for example by adding methanol. A precipitate obtained in this manner was found to contain, in the form of the sodium salts, 3.9% of iminodiacetic acid, 0.4% of fumaric acid, 1.1% of maleic acid and 1.5% of asparagidiacetic acid. The IR spectrum (KBr pellet) had bands at 1720 cm$^{-1}$ (CO ester vibration) and at 1600 cm$^{-1}$ (carboxylate, aminocarboxylate vibration). Hydrogenation iodine number: 10.

EXAMPLE 2

The reaction was carried out with the polyglycerol maleate obtained as described in Example 1a. The resulting 70% strength aqueous solution, cooled to 10°-15° C., was then brought to pH 7 with 40% strength aqueous NaOH. Thereafter an aqueous neutralized solution of an amount of iminodiacetic aicd equimolar to the ester groups present was then added dropwise within said temperature range of from 10° to 15° C. over 30 minutes. The solution was then brought to pH 10 by the addition of sodium carbonate and the remaining sodium hydroxide solution, and the reaction was continued as described under 1b. The resulting sodium salt solution contained as minor components 3.7% of iminodiacetic acid, 0.4% of fumaric acid, 2.3% of maleic acid and 1.1% of asparagicdiacetic acid in the form of the sodium salts.

EXAMPLE 3

Example 1a was repeated to convert a polyglycerol having an average degree of condensation n=2.1 (OH number=1364 mg of KOH/g) into the polyglycerol maleate. The resulting pale yellow 70% aqueous solution of polyglycerol maleate had a saponification number of 800 mg of KOH/g and an acid number of 444 mg of KOH/g (each calculated for 100%). The level of free maleic acid by HPLC was 3.7%. The ester solution was reacted with sodium iminodiacetate as described in Example 1b.

EXAMPLE 4

A polyglycerol maleate was prepared as described in Example 1a. However, the resulting yellow oil was not admixed with water but reacted with iminodiacetatic acid as follows. 226 g (1.7 mol) of iminodiacetic acid were suspended in 250 g of water. The suspension was brought to pH with 277 g of 40% strength aqeous NaOH. After 90 g of sodium carbonate had been added, 259 g of the above-prepared polyglycerol maleate were added a little at a time with vigorous stirring at 10°-15° C. over 30 minutes during which the suspension was maintained at pH 10 by the dropwise addition of 235 g of 40% aqueous NaOH. This was followed by a further 3 hours of stirring at 25° C.

HPLC data of the resulting solution: 3.5% of sodium iminodiacetate, 2.8% of sodium asparagate-diacetate, 1.5% of sodium maleate and 2.1% of sodium fumarate.

After 1.5 l of methanol had been added, the resulting precipitate was filtered off with suction and dried. HPLC: 3.9% of iminodiacetic acid, 3.8% of asparagicdiacetic acid, 0.5% of maleic acid 0.225% of fumaric acid, each as sodium salt. Hydrogenation iodine number: 12.

EXAMPLE 5

66.5 g (0.5 mol) of asparagic acid were suspended in 70 g water. The suspension was brought to pH 9.5 with 77 g of 40% strength aqueous sodium hydroxide solution. After 25 g of sodium carbonate had been added, 118 g of a 70% aqueous polyglycerol maleate mixture syntesized as described in Example 1a) were added dropwise with vigorous stirring at 10°-15° C. over 30 minutes during which the pH was maintained at 9.5 by the addition of 72 g of 40% aqueous NaOH. The reaction mixture was then stirred at 25° C. for a further 2 hours. The resulting sodium salt solution was neutralized at 10°-15° C. with 50% strength sulfuric acid and then spray dried.

The spray dried product was 60% the formally iminodisuccinated polyglycerol derivative of the formula I where $$R = -\underset{\underset{O}{\|}}{C}-CH_2-\underset{\underset{COOX}{|}}{CHL}$$

$$L = -NH-\underset{\underset{CH_2-COOX}{|}}{CH-COOX}$$

X=Na and
n=2.8.

EXAMPLE 6

To 69 g of a polyglycerol maleate synthesized as described in Example 1a, in 70% aqueous solution, were added at 15°-20° C. with vigorous stirring 42.3 g of the sodium salt of ethanolaminoacetic acid (0.3 mol). After 40 g of water had been added, 16 g of sodium carbonate were added a little at a time at 10°-15° C. over 10 minutes, followed by 66 g of 40% strength aqueous sodium hydroxide, solution added dropwise over 30 minutes. The result was a pH of 10. The reaction mixture was then stirred at 25° C. for 2.5 hours. The result was a clear aqueous sodium salt solution.

The product of the formula I where $$R = -\underset{\underset{O}{\|}}{C}-CH_2-\underset{\underset{COOX}{|}}{CHL}$$

$$L = -\underset{\underset{CH_2-CH_2-OH}{|}}{N}-CH_2-COOX$$

X=Na and
n=2.8 was precipitated by the addition of 700 ml of methanol, filtered off, washed with methanol and dried. It contained, in each case as the sodium salt, 1.3% of ethanolaminoacetic acid, 2.8% of the formal adduct of ethanolaminoacetic acid with maleic acid, 0.3% f fumaric acid and 1.5% of maleic acid. The yield was 213 g.

EXAMPLE 7

Example 6 was repeated using sodium sarcosinate instead of sodium ethanolaminoacetate. Precipitation with methanol and drying gave a product of the formula I where $$R = -\underset{\underset{O}{\|}}{C}-CH_2-\underset{\underset{COOX}{|}}{CHL}$$

$$L = -\underset{\underset{CH_3}{|}}{N}-CH_2-COOX$$

X=Na and
n2.8.

It also contained 2.3% of sarcosine, 3.8% of the formal adduct of sarcosine with maleic acid, 0.3% of fumaric acid and 1.6% of maleic acid, each in the form of the sodium salt.

EXAMPLE 8

169 g (1.0 mol) of sodium glutamate were dissolved in 220 g of water. 53 g of sodium carbonate were added, followed at 10°-15° C. by 217 g of a 70% strength solution of a polyglycerol maleate synthesized as described in Example 1a, added dropwise in the course of 30 minutes with vigorous stirring.

At the same time, a total of 187 g of 25% strength sodium hydroxide solution were added to maintain the pH at 9.5. The reaction mixture was then stirred at 25° C. for 2.5 hours. The result was a clear aqueous sodium salt solution of a polyglycerol maleate glutamate of the formula I where

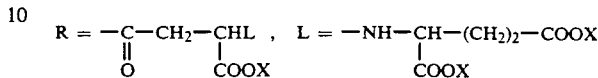

X=Na and n=2.8. The addition product of sodium glutamate with the abovementioned polyglycerol maleate was precipitated by adding 900 ml of methanol, filtered off, washed with methanol and dried. It contained as impurities, each case in the form of the sodium salts, 5.3% of glutamic acid, 4.1% of the formal adduct of glutamic acid with maleic acid, 0.8% of fumaric acid and 2.8% of maleic acid. The addition product thus prepared (a polyglycerol maleate glutamate) is an effective complexing agent for heavy metal and alkaline earth metal ions which is very readily biodegradable.

APPLICATION TESTING

Determination of the calcium carbonate dispersing capacity

The calcium carbonate dispersing capacity is determined by dissolving 1 g of the polymer in 100 ml of distilled water neutralizing if necessary by the addition of 1 g of sodium hydroxide solution, and adding 10 ml of 10% strength sodium carbonate solution. The solution is subsequently titrated with 0.25 M calcium acetate solution at a constant pH and temperature. The pH is set by the addition of either dilute sodium hydroxide solution or dilute hydrochloric acid solution. The dispersing capacity is determined at 20° C. and pH 11 and at 80° C. and pH 10. The results are shown in the following table:

| Polymer | Product of Example No. | Dispersing capacity of polymer [mg of CaCO₃/g of polymer as Na salt] | |
|---|---|---|---|
| | | 20° C./pH 11 | 80° C./pH 10 |
| Oligoglycerol/ maleic anhydride/ iminodiacetic acid | 3 | 180 | 130 |
| Oligoglycerol/ maleic anhydride/ iminodiacetic acid | 1 | 210 | 120 |
| Oligoglycerol/ maleic anhydride/ iminodiacetic acid | 2 | 190 | 90 |
| Oligoglycerol/ maleic anhydride/ iminodiacetic acid | 4 | 180 | 80 |
| Homopolyacrylate K value 30 | Comparison | 115 | 55 |

DETERMINATION OF CLAY DISPERSING POWER

A 100 ml graduated cylinder is filled with 1 g of china clay (SPS 151), 100 ml of distilled water and 10 ppm of polymer (as 100% sodium salt). The dispersion is intensively mixed with a suitable stirrer and then stored for 3 hours. After 3 hours, a 2.5 ml sample is taken from the middle of the graduated cylinder and diluted with distilled water to 25 ml, and the turbidity of the sample is determined by means of a photometer. The turbidity is reported in normal turbidity units. The stabler the dispersion is, the higher the number of normal turbidity units obtained.

| Polymer | Product of Example No. | Normal turbidity units |
|---|---|---|
| Without | | 50 |
| Oligoglycerol/ maleic anhydride/ iminodiacetic acid | 4 | 360 |
| Oligoglycerol/ maleic anhydride/ iminodiacetic acid | 1 | 370 |
| Oligoglycerol/ maleic anhydride/ iminodiacetic acid | 3 | 350 |
| Oligoglycerol/ maleic anhydride/ iminodiacetic acid | 2 | 350 |
| Homopolyacrylate K value 30 | | 300 |

Distinct improvements over the state of the art (homopolyacrylate) are evident not only in calcium carbonate dispersing capacity but also in clay dispersing power.

We claim:

1. A glycerol aminocarboxylate of formula

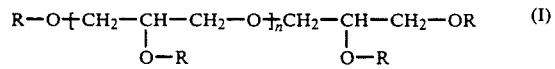

where
n is from 0 to 10 and
R is

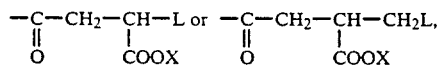

where
L is iminodiacetate, asparate, glutamate, sarcosinate, glycinate, serinate, hydroxyaspartate, ethanolaminoacetate, diethanolamino, alanate or taurinate and
X is hydrogen, an alkali metal, ammonium or substituted ammonium.

2. A glycerol aminocarboxylate of formula I as claimed in claim 1, where L is iminodiacetate and n is from 1 to 4.

3. A process for preparing a compound of the formula I as claimed in claim 1, where comprises esterifying
(a) a compound of formula

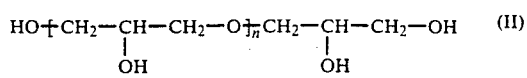

where n is from 0 to 10, with
(b) maleic anhydride, itaconic anhydride, a maleic half-ester or an itaconic half-ester to give a compound of the formula

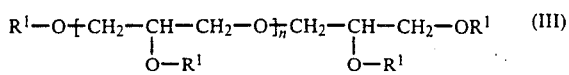

where
$R^1$ is

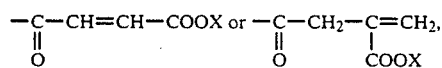

and then reacting the compound of the formula III with a compound of the formula

where L is as defined in claim 1, in a weakly alkaline aqueous medium to give a compound of the formula I.

4. A process as claimed in claim 3, wherein a compound of the formula II is esterified with maleic anhydride in the form of a viscous melt in the absence of a solvent, sufficient water is then added to produce a 50–80% strength by weight aqueous solution, and this solution is then reacted with a compound of the formula IV to give a compound of the formula I.

5. A process as claimed in claim 3, wherein a compound of the formula II is esterified at 80°–140° C. with the exclusion of water, sufficient water is then added to produce a 50–80% strength by weight aqueous solution, and this solution is then reacted with glutamic acid to form a compound of the formula I.

6. A process as claimed in claim 3, wherein the reaction of III with IV to give I is carried out at pH 7.5–11 and at 10°–70° C.

7. A process as claimed in claim 3, wherein the reaction of a compound of the formula III with a compound of the formula IV is carried out at pH 9°–10° and 10°–40° C.

* * * * *